(12) United States Patent
Kamimura et al.

(10) Patent No.: US 9,307,910 B2
(45) Date of Patent: Apr. 12, 2016

(54) OPTICAL MEASUREMENT APPARATUS AND ENDOSCOPE SYSTEM

(71) Applicant: OLYMPUS CORPORATION, Tokyo (JP)

(72) Inventors: Kenji Kamimura, Hachioji (JP); Takeshi Suga, Hino (JP); Yuki Shono, Evanston, IL (US); Hideyuki Takaoka, Hachioji (JP); Ryosuke Ito, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 14 days.

(21) Appl. No.: 14/099,453

(22) Filed: Dec. 6, 2013

(65) Prior Publication Data

US 2014/0180131 A1 Jun. 26, 2014

Related U.S. Application Data

(63) Continuation of application No. PCT/JP2013/060555, filed on Apr. 5, 2013.

(60) Provisional application No. 61/622,257, filed on Apr. 10, 2012.

(51) Int. Cl.
*A61B 5/00* (2006.01)
*A61B 1/06* (2006.01)
*A61B 1/00* (2006.01)

(52) U.S. Cl.
CPC ............. *A61B 5/0075* (2013.01); *A61B 1/0638* (2013.01); *A61B 1/0661* (2013.01); *A61B 5/0084* (2013.01); *A61B 1/00186* (2013.01)

(58) Field of Classification Search
CPC .. A61B 1/0638; A61B 1/0661; A61B 5/0075; A61B 5/0084
See application file for complete search history.

(56) References Cited

U.S. PATENT DOCUMENTS

| 5,749,830 A | * | 5/1998 | Kaneko et al. ................ 600/160 |
| 2008/0037024 A1 | | 2/2008 | Backman et al. |

FOREIGN PATENT DOCUMENTS

| JP | A-02-299634 | 12/1990 |
| JP | A-03-163410 | 7/1991 |

(Continued)

OTHER PUBLICATIONS

Mar. 7, 2014 Decision of a Patent Grant issued in Japanese Application No. 2013-554721 (with translation).

(Continued)

*Primary Examiner* — Amanda Lauritzen Moher
(74) *Attorney, Agent, or Firm* — Oliff PLC

(57) ABSTRACT

An endoscope system includes: an endoscope with a unit to be inserted into a subject and captures an inside image of the subject by an imaging unit provided in the unit to generate an image signal; an optical apparatus including a measurement probe to be inserted into the subject through the unit; an endoscope unit that switches between observation light of a plurality of wavelengths and outputs the observation light to observe a target object from the unit; a probe unit that outputs measurement light to measure characteristics of the target object via the measurement probe; a light unit that receives return light via the measurement probe, the return light caused by reflection and/or scattering of the measurement light on the target object; and a switching unit that switches a wavelength band of the measurement light to a different wavelength band from the observation light outputted by the endoscope unit.

2 Claims, 13 Drawing Sheets

(56) References Cited

FOREIGN PATENT DOCUMENTS

| JP | A-04-297222 | 10/1992 |
| JP | A-09-248281 | 9/1997 |
| JP | A-2001-137187 | 5/2001 |
| JP | A-2009-537014 | 10/2009 |
| JP | A-2010-063839 | 3/2010 |
| JP | A-2010-227200 | 10/2010 |

OTHER PUBLICATIONS

Partial translation of Jan. 21, 2014 Office Action issued in Japanese Application No. 2013-5547218.

Jul. 9, 2013 International Search Report issued in International Application No. PCT/JP2013/060555 (with translation).

* cited by examiner (a) ENDOSCOPE LIGHT SOURCE DEVICE (b) OPTICAL MEASUREMENT APPARATUS

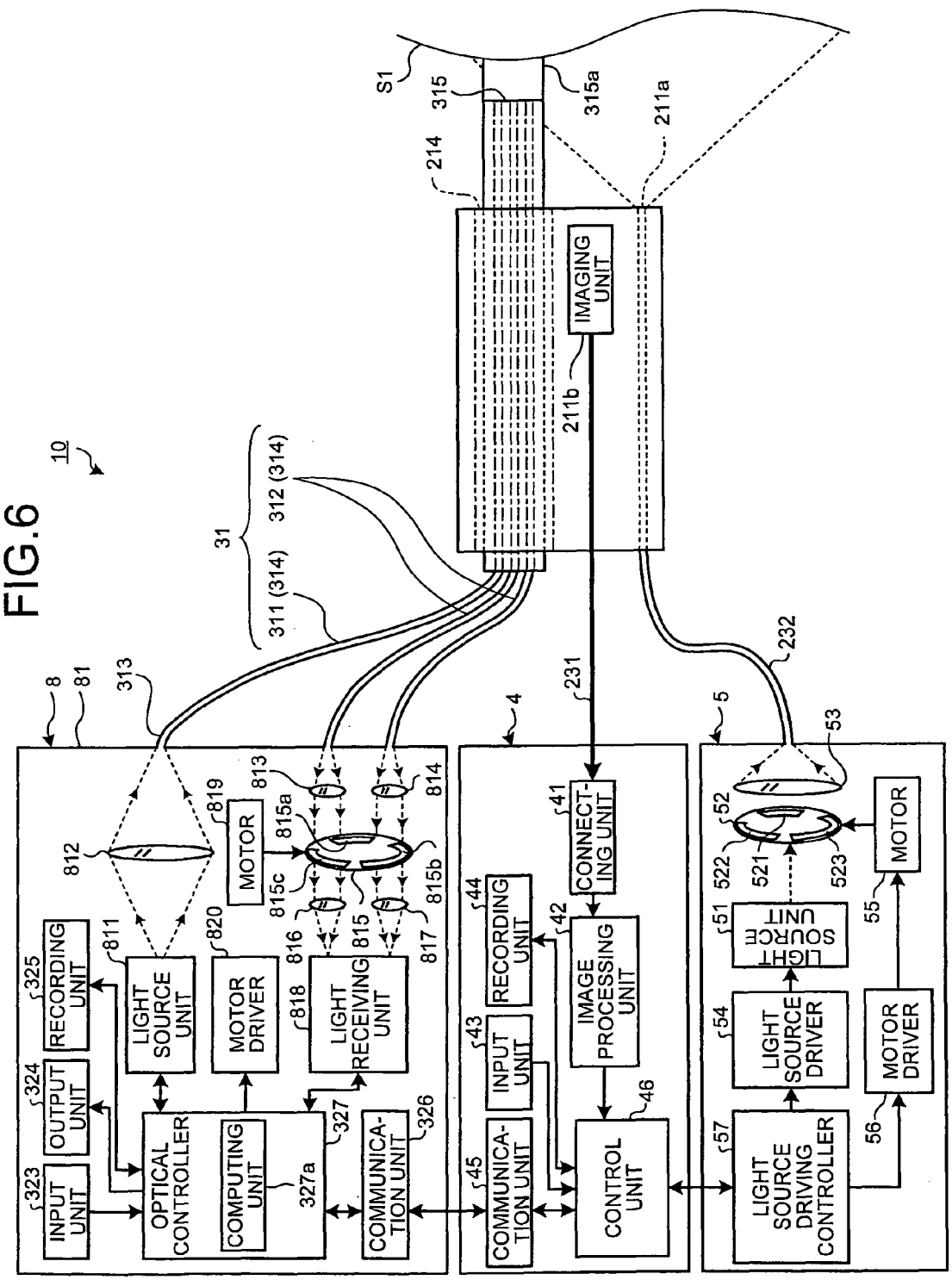

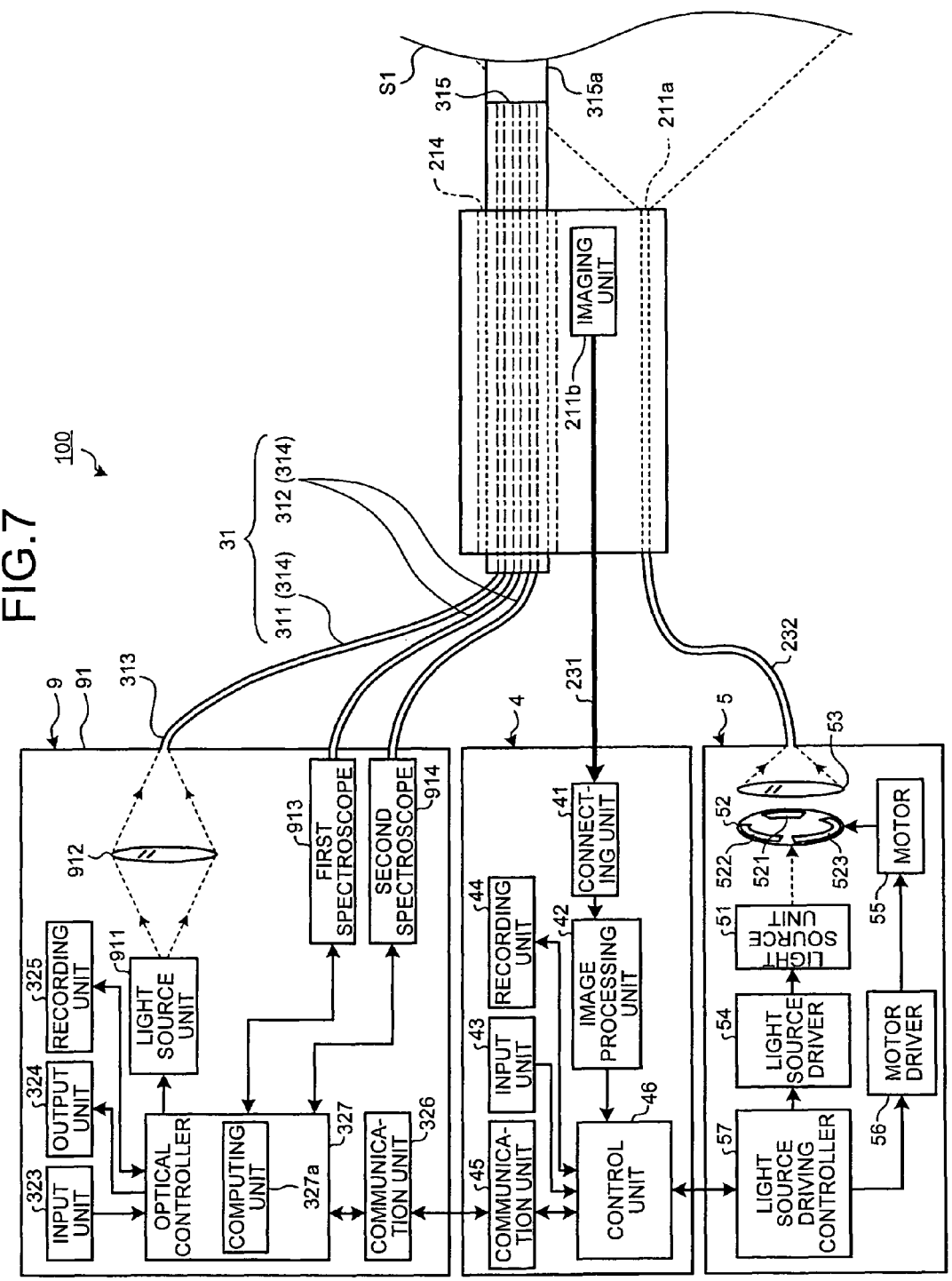

OPTICAL MEASUREMENT APPARATUS AND ENDOSCOPE SYSTEM

CROSS-REFERENCE TO RELATED APPLICATIONS

This application is a continuation of PCT international application Ser. No. PCT/JP2013/060555 filed on Apr. 5, 2013 which designates the United States, incorporated herein by reference, and which claims the benefit of priority from U.S. provisional application No. 61/622,257 filed on Apr. 10, 2012, incorporated herein by reference.

BACKGROUND OF THE INVENTION

1. Field of the Invention

The present invention relates to an optical measurement apparatus and an endoscope system for irradiating body tissues with illumination light and estimating characteristics of the body tissues based on a measurement value of return light caused by reflection and/or scattering of the illumination light on the body tissues.

2. Description of the Related Art

Conventionally, an optical measurement apparatus is known which radiates illumination light on body tissues, and estimates the characteristics of the body tissues based on a measurement value of detection light reflected or scattered from the body tissues. This optical measurement apparatus is used in combination with an endoscope which observes an organ such as a digestive organ. As such an optical measurement apparatus, an optical measurement apparatus is proposed which uses LEBS (Low-Coherence Enhanced Backscattering) technology of detecting the characteristics of the body tissues by radiating low-coherent white light of a short spatial coherence length on the body tissues from a distal end of a radiating fiber of a probe, and measuring an intensity distribution of light scattering at a plurality of angles, using a plurality of light receiving fibers.

Further, a technique is known which performs spectrometric measurement of the mucous membrane of the biological body using an endoscope (see Japanese Patent Application Laid-open No. 2010-063839). With this technique, when a measurement probe which performs spectrometric analysis detects near-infrared light, by controlling an illumination range such that the observation light of the endoscope is not radiated on an observation portion of the measurement probe, the measurement probe is prevented from detecting observation light from the endoscope.

Further, a technique is known which prevents the probe from analyzing observation light from the endoscope by stopping radiation of observation from the endoscope while the probe is performing spectrometric analysis (see Japanese Patent Application Laid-open No. 9-248281).

SUMMARY OF THE INVENTION

An endoscope system according to one aspect of the invention includes: an endoscope which includes an insertion unit configured to be inserted into an inside of a subject and which is configured to capture an image of the inside of the subject by an imaging unit provided in the insertion unit and generate an image signal; an optical measurement apparatus including a measurement probe configured to be inserted into the inside of the subject through the insertion unit; an endoscope light source unit configured to switch between observation light of a plurality of wavelengths and output the observation light to observe a target object from the insertion unit; a probe light source unit configured to output measurement light to measure characteristics of the target object via the measurement probe; a light receiving unit configured to receive return light via the measurement probe, the return light being caused by reflection and/or scattering of the measurement light on the target object; and a switching unit configured to switch a wavelength band of the measurement light to a wavelength band different from that of the observation light outputted by the endoscope light source unit. The light receiving unit includes a spectroscope configured to receive and disperse the return light. The switching unit includes: a computing unit configured to compute the characteristics of the target object based on results of dispersion by the spectroscope; and a control unit configured to switch a wavelength band of the return light used for computing by the computing unit in such a way that the wavelength band of the observation light outputted by the endoscope light source unit and the wavelength band of the return light used for computing by the computing unit are different from one another.

An endoscope system according to another aspect of the invention includes: an endoscope which includes an insertion unit configured to be inserted into an inside of a subject and which is configured to capture an image of the inside of the subject by an imaging unit provided in the insertion unit and generate an image signal; an optical measurement apparatus including a measurement probe configured to be inserted into the inside of the subject through the insertion unit; an endoscope light source unit configured to switch between observation light of a plurality of wavelengths and output the observation light to observe a target object from the insertion unit; a probe light source unit configured to output measurement light to measure characteristics of the target object via the measurement probe; a light receiving unit configured to receive return light via the measurement probe, the return light being caused by reflection and/or scattering of the measurement light on the target object; and a switching unit configured to switch a wavelength band of the measurement light to a wavelength band different from that of the observation light outputted by the endoscope light source unit. The endoscope light source unit is configured to sequentially output the observation light of different wavelength bands. The switching unit includes: a rotation filter which is planar shaped and includes a plurality of filters which allow transmission of specified wavelength bands; a driving unit configured to rotate the rotation filter; and a control unit configured to control the rotation filter to rotate by controlling driving by the driving unit, in such a way that the wavelength band of the observation light outputted by the endoscope light source unit and a wavelength band of the return light received by the light receiving unit are different from one another.

An optical measurement apparatus according to still another aspect of the invention includes a measurement probe configured to be inserted through an insertion unit of an endoscope, and is configured to perform bidirectional communication with a control device for controlling an endoscope light source device having an endoscope light source unit configured to switch between observation light of a plurality of wavelengths and output the observation light to the endoscope. The optical measurement apparatus includes: a probe light source unit configured to output measurement light to measure characteristics of a target object via the measurement probe; a light receiving unit configured to receive return light via the measurement probe, the return light being caused by reflection and/or scattering of the measurement light on the target object; a computing unit configured to compute a characteristic value of the target object based on results of light receiving by the light receiving unit;

and a switching unit configured to switch a wavelength band of the measurement light, based on a driving signal transmitted from the control device, in such a way that the wavelength band of the measurement light is different from that of the observation light outputted by the endoscope light source unit. The light receiving unit includes a spectroscope configured to receive and disperse the return light. The switching unit includes: a computing unit configured to compute the characteristics of the target object based on results of dispersion by the spectroscope; and a control unit configured to switch a wavelength band of the return light used for computing by the computing unit in such a way that the wavelength band of the observation light outputted by the endoscope light source unit and the wavelength band of the return light used for computing by the computing unit are different from one another.

An optical measurement apparatus according to still another aspect of the invention includes a measurement probe configured to be inserted through an insertion unit of an endoscope, and is configured to perform bidirectional communication with a control device for controlling an endoscope light source device having an endoscope light source unit configured to switch between observation light of a plurality of wavelengths and output the observation light to the endoscope. The optical measurement apparatus includes: a probe light source unit configured to output measurement light to measure characteristics of a target object via the measurement probe; a light receiving unit configured to receive return light via the measurement probe, the return light being caused by reflection and/or scattering of the measurement light on the target object; a computing unit configured to compute a characteristic value of the target object based on results of light receiving by the light receiving unit; and a switching unit configured to switch a wavelength band of the measurement light, based on a driving signal transmitted from the control device, in such a way that the wavelength band of the measurement light is different from that of the observation light outputted by the endoscope light source unit. The switching unit includes: a rotation filter which is planar shaped and includes a plurality of filters which allow transmission of specified wavelength bands; a driving unit configured to rotate the rotation filter; and a control unit configured to control the rotation filter to rotate by controlling driving by the driving unit, in such a way that the wavelength band of the observation light outputted by the endoscope light source unit and a wavelength band of the return light received by the light receiving unit are different from one another.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 6 is a block diagram schematically illustrating a configuration of an endoscope system according to a third embodiment of the present invention;

FIG. 7 is a block diagram schematically illustrating a configuration of an endoscope system according to a fourth embodiment of the present invention;

DETAILED DESCRIPTION OF THE PREFERRED EMBODIMENTS

Figure 1:
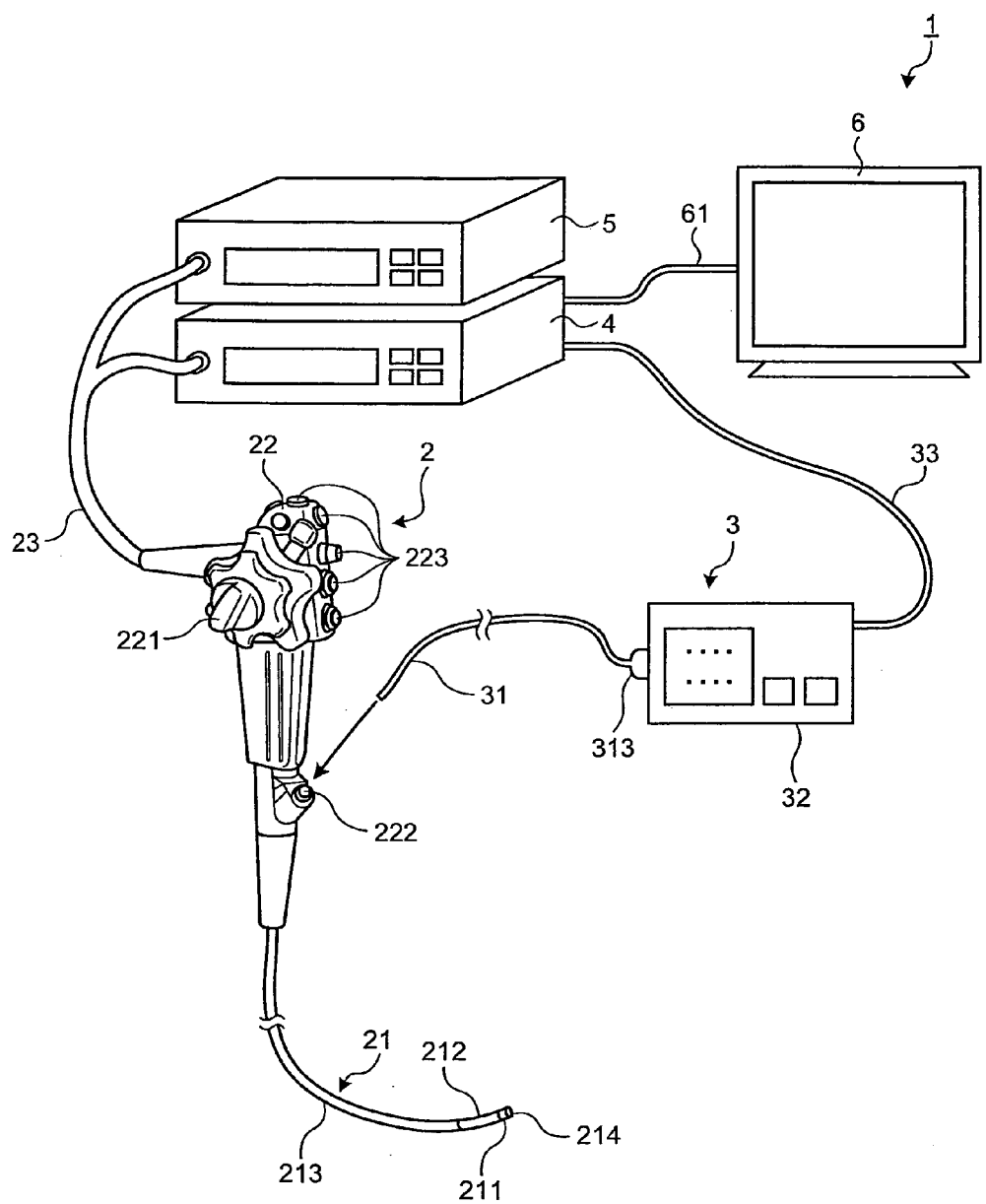
FIG. 1 is a view illustrating a schematic configuration of an endoscope system according to the first embodiment of the present invention.

Hereinafter, preferred embodiments of an optical measurement apparatus and an endoscope system according to the present invention will be described in details with reference to the drawings, using an optical measurement apparatus which uses LEBS technology as an example. Further, the present invention is by no means limited to these embodiments. Further, the same reference numerals will be used to refer to the same components in the drawings. Further, drawings are schematic, and it needs to be noted that, for example, the relationship between the thickness and the width of each member and the ratio of each member are actually different. Further, dimensions or ratios are different between the mutual drawings.

First Embodiment

FIG. 1 is a view illustrating a schematic configuration of an endoscope system according to a first embodiment of the present invention. As illustrated in FIG. 1, an endoscope system 1 according to the first embodiment has: an endoscope device 2 (endoscope) which is introduced to an interior of a subject, and generates an image signal of the interior of the subject by capturing an image of an inside of a body of the subject; an optical measurement apparatus 3 which is introduced to the interior of the subject through the endoscope device 2, and estimates the characteristics of body tissues in the interior of the subject; an endoscope light source device 5 which generates observation light of the endoscope device 2; a control device 4 (processor) which performs specified image processing of an image signal captured by the endoscope device 2, and controls each unit of the endoscope system 1; and a display device 6 which displays an image matching the image signal for which the control device 4 performs image processing.

The endoscope device 2 has: an insertion unit 21 which is inserted to the interior of the subject; an operating unit 22 which is provided on a side of a proximal end portion of the insertion unit 21; and a flexible universal cord 23 which extends from a side portion of the operating unit 22.

The insertion unit 21 is realized using, for example, an illumination fiber (light guide cable) and an electrical cable. The insertion unit 21 has: a distal end portion 211 which has an imaging unit in which a CCD sensor or a CMOS sensor is built as an image sensor which captures an image of the interior of the subject; a curved portion 212 which is formed with a plurality of curved sections and which can be curved; and a flexible tube portion 213 which is provided on the side of a proximal end portion of the curved portion 212 and has flexibility. The distal end portion 211 has: an illuminating unit which illuminates the interior of the subject through an illuminating lens; an observing unit which captures an image of the interior of the subject; an aperture portion 214 which communicates with a treatment tool channel and an air-supply/water supply nozzle (not illustrated).

The operating unit 22 has: a curved knob 221 which curves the curved portion 212 in up and down directions and left and right directions; a treatment tool insertion unit 222 in which a processing tool such as a biopsy forceps, a laser surgical knife, or a measurement probe of the optical measurement apparatus 3 is inserted in a body cavity of the subject; and a plurality of switches 223 which operate peripheral devices such as the optical measurement apparatus 3, the endoscope light source device 5, the control device 4, an air-supply device, a water-supply device and a gas-supply device. The treatment tool inserted from the treatment tool insertion unit 222 passes the treatment tool channel provided therein, and appears from the aperture portion 214 at the distal end of the insertion unit 21.

The universal cord 23 is formed using, for example, the illumination fiber and the electrical cable. The universal cord 23 transmits observation light emitted from the endoscope light source device 5 to the distal end portion 211 through the operating unit 22 and the flexible tube portion 213. The universal cord 23 transmits an image signal captured by the imaging unit, such as an imaging device, provided at the distal end portion 211, to the control device 4.

The optical measurement apparatus 3 has: a measurement probe 31 which is inserted to the inside of the body of the subject through the treatment tool insertion unit 222 of the endoscope device 2; a main body unit 32 which estimates the characteristics (characteristic value) of the measurement target by outputting measurement light to the measurement probe 31 and receiving return light caused by reflection and/or scattering of the measurement light on a measurement target through the measurement probe 31; and a transmission cable 33 which transmits, for example, a measurement result of the main body unit 32 to the control device 4.

The control device 4 applies specified image processing to the image signal of the subject transmitted through the universal cord 23 and captured by the distal end portion 211 of the endoscope device 2. The control device 4 records a measurement result of the optical measurement apparatus 3 transmitted through the transmission cable 33. The control device 4 controls each unit of the endoscope system 1, based on various command signals transmitted from the switches 223 in the operating unit 22 of the endoscope device 2 through the universal cord 23.

The endoscope light source device 5 is formed using, for example, a white light source or a special light source. The endoscope light source device 5 supplies light from the white light source or the special light source, to the endoscope device 2 connected through the illumination fiber of the universal cord 23 as observation light (illumination light).

The display device 6 is formed using, for example, a liquid crystal or organic electro luminescence (EL) display. The display device 6 displays, for example, an image matching the image signal for which the control device 4 performs specified image processing and the measurement result of the optical measurement apparatus 3, through a video cable 61. By this means, by operating the endoscope device 2 while looking at the image displayed by the display device 6, the operator can observe a desired position of the interior of the subject and determine the characteristics.

Figure 2:
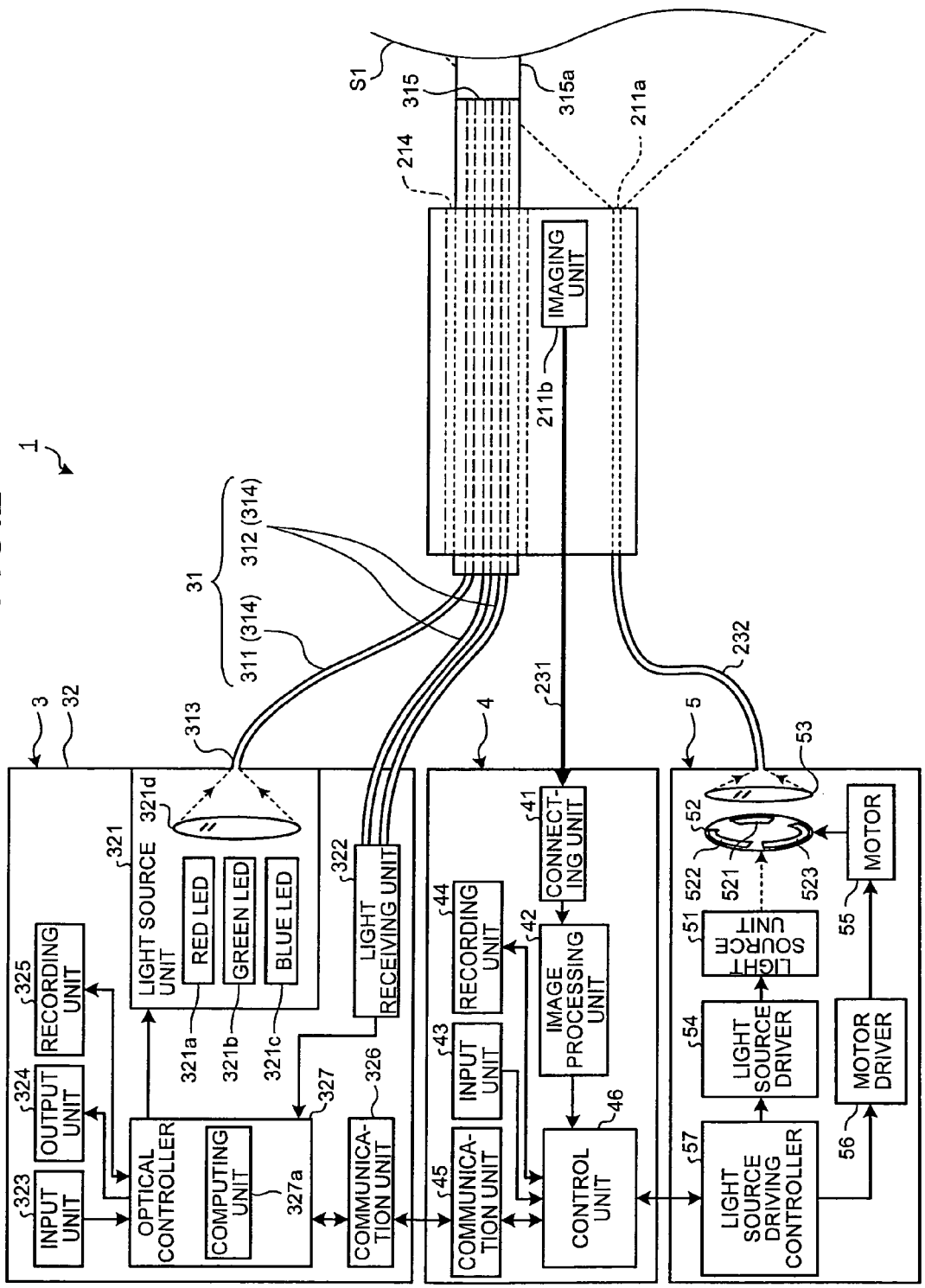
FIG. 2 is a block diagram schematically illustrating configurations of an optical measurement apparatus, an endoscope light source and a control device illustrated in FIG. 1.

Next, detailed configurations of the optical measurement apparatus 3, the control device 4 and the endoscope light source device 5 described with reference to FIG. 1 will be described. FIG. 2 is a block diagram schematically illustrating configurations of the optical measurement apparatus 3, the control device 4 and the endoscope light source device 5 in FIG. 1.

First, the detailed configuration of the optical measurement apparatus 3 will be described. The optical measurement apparatus 3 has the measurement probe 31, and the main body unit 32.

The measurement probe 31 is realized using, for example, one or a plurality of optical fibers. For example, the measurement probe 31 is realized using an illumination fiber 311 which emits measurement light (illumination light) to body tissues S1 that are a measurement target, and a plurality of light receiving fibers 312 on which return light caused by reflection and/or scattering of the measurement light on the measurement target are incident at different angles (scattering angles). At least distal end portions of the illumination fiber 311 and the light receiving fibers 312 are aligned in parallel to each other. The measurement probe 31 has a proximal end portion 313, a flexible portion 314 and a distal end portion 315.

The proximal end portion 313 is connected detachably to the main body unit 32. The flexible portion 314 has flexibility, and transmits measurement light (illumination light) emitted from the main body unit 32, to the distal end portion 315 including the distal end at which the end surface of the illumination fiber 311 is exposed, and transmits the return light of the measurement light which is incident through the distal end portion 315, to the main body unit 32. The distal end portion 315 emits measurement light transmitted from the flexible portion 314, to the body tissues S1, and return light caused by reflection and and/or scattering of the measurement light on the body tissues S1 are incident on the distal end portion 315. The distal end portion 315 has a permeable rod 315a as an optical member. The rod 315a has a columnar shape to fix the distances between a surface of the body tissues S1 and the distal ends of the illumination fiber 311 and the light receiving fibers 312. In addition, although the measurement probe 31 having the two light receiving fibers 312 has been described as an example with reference to FIG. 2, at least two or more types of light scattering at different scattering angles need to be received, and therefore the number of light receiving fibers 312 may be three or more. Furthermore, the number of illumination fiber 311 can be appropriately changed depending on the body tissues S1 that are a measurement target.

The main body unit 32 has a light source unit 321, a light receiving unit 322, an input unit 323, an output unit 324, a recording unit 325, a communication unit 326 and an optical controller 327.

The light source unit 321 generates light to radiate the body tissues S1. The light source unit 321 sequentially switches between a plurality of measurement light of different wavelength bands and outputs the measurement light to the measurement probe 31. More specifically, the light source unit 321 has: a red LED (Light Emitting Diode) 321a which emits red light; a green LED 321b which emits green light; a blue LED 321c which emits blue light; and one or a plurality of condenser lens 321d which focuses light emitted by each LED and supplies light to the measurement probe 31. Under control of the optical controller 327, the light source unit 321 makes one of the red LED 321a, the green LED 321b and the blue LED 321c emit light to sequentially switch between the measurement light of different wavelength bands and the measurement light is output to the measurement probe 31. In addition, the light source unit 321 may make the red LED 321a, the green LED 321b and the blue LED 321c emit light at the same time to radiate on the measurement probe 31.

The light receiving unit 322 receives the return light caused by reflection and/or scattering of the measurement light, which is outputted from the measurement probe 31, on the body tissues S1. The light receiving unit 322 is realized using a plurality of spectrometric measuring instruments. The light receiving unit 322 measures spectrum components and intensity distributions of return light caused by reflection and/or scattering of the measurement light outputted from the measurement probe 31, and measures each wavelength. The light receiving unit 322 outputs the measurement result to the optical controller 327.

The input unit 323 is realized using, for example, a push-type switch or a touch panel, and, when the switch is operated, receives and outputs an input of command information for activating the optical measurement apparatus 3 or operation information for commanding various operations, to the optical controller 327.

The output unit 324 is realized using, for example, a liquid crystal or organic EL display and a speaker, and outputs information related to various processing in the optical measurement apparatus 3.

The recording unit 325 is realized using volatile memory or non-volatile memory, and records various programs for operating the optical measurement apparatus 3 and various items of data and various parameters used for optical measurement processing. The recording unit 325 temporarily records information which is being processed by the optical measurement apparatus 3.

The communication unit 326 is a communication interface for communicating with the control device 4 through the transmission cable 33. The communication unit 326 transmits the measurement result of the optical measurement apparatus 3 to the control device 4, and outputs a command signal or a control signal transmitted from the control device 4, to the optical controller 327.

The optical controller 327 is configured using, for example, a CPU (Central Processing Unit). The optical controller 327 controls a processing operation of each unit of the optical measurement apparatus 3. The optical controller 327 transfers command information for each configuration of the optical measurement apparatus 3 or data to control the operation of the optical measurement apparatus 3. The optical controller 327 records the measurement result from the light receiving unit 322, in the recording unit 325. The optical controller 327 has a computing unit 327a. The computing unit 327a performs a plurality of computation processing based on the measurement result from the light receiving unit 322, and computes a characteristic value related to the characteristics of the body tissues S1. The type of this characteristic value is set according to, for example, command information received by the input unit 323.

Next, the control device 4 will be described. The control device 4 has a connecting unit 41, an image processing unit 42, an input unit 43, a recording unit 44, a communication unit 45 and a control unit 46.

The connecting unit 41 is connected with an electrical cable (communication cable) 231 of the universal cord 23. The connecting unit 41 receives an image signal which is a digital signal captured by an imaging unit 211b arranged near an observation window (not illustrated) of the distal end portion 211, through the electrical cable 231 of the universal cord 23 to output to the image processing unit 42.

The image processing unit 42 performs specified image processing of the image signal outputted from the connecting unit 41 to output to the display device 6. More specifically, the image processing unit 42 performs image processing including at least optical black subtraction processing, white balance (WB) adjustment processing, concurrent processing of an image signal when the image sensor is provided in a Bayer pattern, color matrix computation processing, gamma correction processing, color reproduction processing and edge emphasis processing for an image signal (image data). The image processing unit 42 converts the image signal to which image processing is applied, from a digital signal into an analog signal, and changes the image signal of the converted analog signal to a format such as a high-definition type to output to the display device 6. By this means, the display device 6 displays one in-vivo image.

The input unit 43 is realized using an operation device such as a mouse, a keyboard and a touch panel, and receives inputs of various pieces of command information of the endoscope system 1. More specifically, the input unit 43 receives inputs of various pieces of command information such as subject information, identification information of the endoscope device 2 and test content.

The recording unit 44 is realized using volatile memory or non-volatile memory, and records various programs for operating the control device 4 and the endoscope light source device 5. The recording unit 44 temporarily records information which is being processed by the control device 4. The recording unit 44 records the image signal for which the image processing unit 42 performs image processing and the measurement result of the optical measurement apparatus 3. In addition, the recording unit 44 may be configured using, for example, a memory card attached from an outside of the control device 4.

The communication unit 45 is a communication interface for communicating with the optical measurement apparatus 3 through the transmission cable 33.

The control unit 46 is realized using, for example, a CPU. The control unit 46 controls a processing operation of each unit of the control device 4. The control unit 46 transfers command information for each configuration of the control device 4 or data to control the operation of the control device 4. The control unit 46 is connected to the endoscope device 2, the optical measurement apparatus 3 and the endoscope light source device 5, respectively through each cable. In the first embodiment, the control unit 46 functions as a switch unit.

Next, the endoscope light source device 5 will be described. The endoscope light source device 5 has a light source unit 51, a rotation filter 52, a condenser lens 53, a light source driver 54, a motor 55, a motor driver 56 and a light source driving controller 57.

The light source unit 51 is formed using, for example, a white LED or a xenon lamp. The light source unit 51 generates observation light (illumination light) to be supplied to the endoscope device 2.

The rotation filter 52 is arranged on an optical path of white light emitted by the light source unit 51, and rotates to allow transmission of only light having a specified wavelength band among observation light emitted by the light source unit 51. More specifically, the rotation filter 52 has a red filter 521, a green filter 522 and a blue filter 523 which allow transmission of light having wavelength bands of red light (R), green light (G) and blue light (B). The rotation filter 52 rotates to allow sequential transmission of light having wavelength bands of red, green and blue (e.g., red: 600 nm to 700 nm, green: 500 nm to 600 nm, and blue: 400 nm to 500 nm). Consequently, the white light emitted by the light source unit 51 can sequentially emit one of red light, green light and blue light for which the band is narrowed, to the endoscope device 2.

The condenser lens 53 is arranged on an optical path of the white light emitted by the light source unit 51, and condenses light having transmitted through the rotation filter 52, to emit to an illumination fiber 232 which is a light guide cable of the universal cord 23.

Under control of the light source driving controller 57, the light source driver 54 supplies specified power to the light source unit 51. By this means, the light emitted from the light source unit 51 is radiated to the outside from an illuminating unit 211a of the distal end portion 211 of the insertion unit 21 through the illumination fiber 232.

The motor 55 is formed using, for example, a stepping motor or a DC motor, and rotates the rotation filter 52. Under control of the light source driving controller 57, the motor driver 56 supplies specified power to the motor 55.

Under control of the control unit 46, the light source driving controller 57 controls the current amount to be supplied to the light source unit 51 and driving of the rotation filter 52, based on a drive signal transmitted from the control unit 46.

Figure 3:
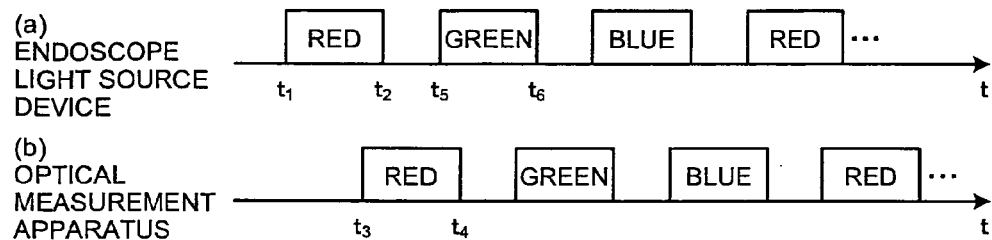
FIG. 3 is a timing chart indicating timings at which the optical measurement apparatus and the endoscope light source device sequentially radiate light of different wavelengths according to the first embodiment of the present invention.

Timings will be described at which the optical measurement apparatus 3 and the endoscope light source device 5 sequentially radiate light of different wavelength bands when the subject is observed in the endoscope system 1 employing the above configuration. FIG. 3 is a timing chart indicating timings at which the optical measurement apparatus 3 and the endoscope light source device 5 sequentially radiate light of different wavelength bands. In FIG. 3, the horizontal axis indicates a time (t).

As illustrated in FIG. 3, the control unit 46 first transmits a drive signal for emitting observation light having a wavelength band of red to the body tissues S1, to the light source driving controller 57. In this case, the light source driving controller 57 drives the light source driver 54 to make the light source unit 51 emit light, and drives the motor 55 through the motor driver 56 to rotate the rotation filter 52 and moves the red filter 521 to the optical path of the white LED. By this means, observation light having the wavelength band of red light is radiated from the distal end portion 211 of the endoscope device 2 to the body tissues S1 (time t1).

Subsequently, the control unit 46 transmits a stop signal for stopping emission of light from the white LED, to the light source driving controller 57, and transmits the drive signal for emitting measurement light having the wavelength band of red color to the body tissues S1, to the optical controller 327 of the optical measurement apparatus 3. In this case, the light source driving controller 57 stops driving of the light source driver 54 and stops emission of light from the light source unit 51 (time t2). By contrast with this, the optical controller 327 of the optical measurement apparatus 3 makes the red LED 321a of the light source unit 321 emit light. By this means, measurement light having the wavelength band of red light is radiated on the body tissues S1 from the illumination fiber 311 of the optical measurement apparatus 3 (time t3).

Subsequently, the control unit 46 transmits a stop signal for stopping emission of light from the red LED, to the optical controller 327 of the optical measurement apparatus 3, and transmits the drive signal for emitting observation light having the wavelength band of green light, to the light source driving controller 57. In this case, the optical controller 327 stops emission of light from the red LED 321a (time t4). By contrast with this, the light source driving controller 57 drives the light source driver 54 to make the light source unit 51 emit light, and drives the motor driver 56 to rotate the rotation filter 52 and moves the green filter 522 to the optical path of the white LED. By this means, observation light having the wavelength band of green light is radiated on the body tissues S1 from the distal end portion 211 of the endoscope device 2 (time t5). In addition, although, in FIG. 3, the optical measurement apparatus 3 and the endoscope light source device 5 radiate light of different wavelength bands without synchronization, the optical measurement apparatus 3 and the endoscope light source device 5 may be synchronized to radiate light having different wavelength bands (for example, the optical measurement apparatus 3 radiates red light and the endoscope light source device 5 radiates blue light).

According to the above-described first embodiment of the present invention, the control unit 46 controls the light source driving controller 57 and the optical controller 327, respectively to switch the endoscope light source device 5 or the light source unit 321 such that the wavelength band of observation light emitted by the endoscope light source device 5 and the wavelength band of measurement light emitted by the light source unit 321 of the optical measurement apparatus 3 are different from each other. As a result, it is possible to perform observation using the endoscope device 2 and measurement using the measurement probe 31 of the optical measurement apparatus 3 at the same time, to cancel the influence of observation light of the endoscope device 2 on measurement using the measurement probe 31, and to perform accurate measurement.

In the first embodiment, by controlling each of the light source driving controller 57 and the optical controller 327, the control unit 46 switches the endoscope light source device 5 or the light source unit 321 such that the wavelength band of the observation light emitted by the endoscope light source device 5 and the wavelength band of the measurement light emitted by the light source unit 321 of the optical measurement apparatus 3 are different from each other. Alternatively, the optical controller 327 may acquire narrow-band information on the wavelength band of the observation light emitted by the endoscope light source device 5 via the control unit 46 and, based on the narrow-band information, the optical controller 327 switches the wavelength band of the measurement light emitted by the light source unit 321 to a different wavelength band.

Second Embodiment

Next, a second embodiment of the present invention will be described. Although the light source unit of the optical measurement apparatus and the endoscope light source device are separately provided with the above first embodiment, the light source unit 321 of the optical measurement apparatus 3 and the endoscope light source device 5 are integrally provided with the second embodiment of the present invention. In addition, the same reference numeral will be used below to refer to the same components.

Figure 4:
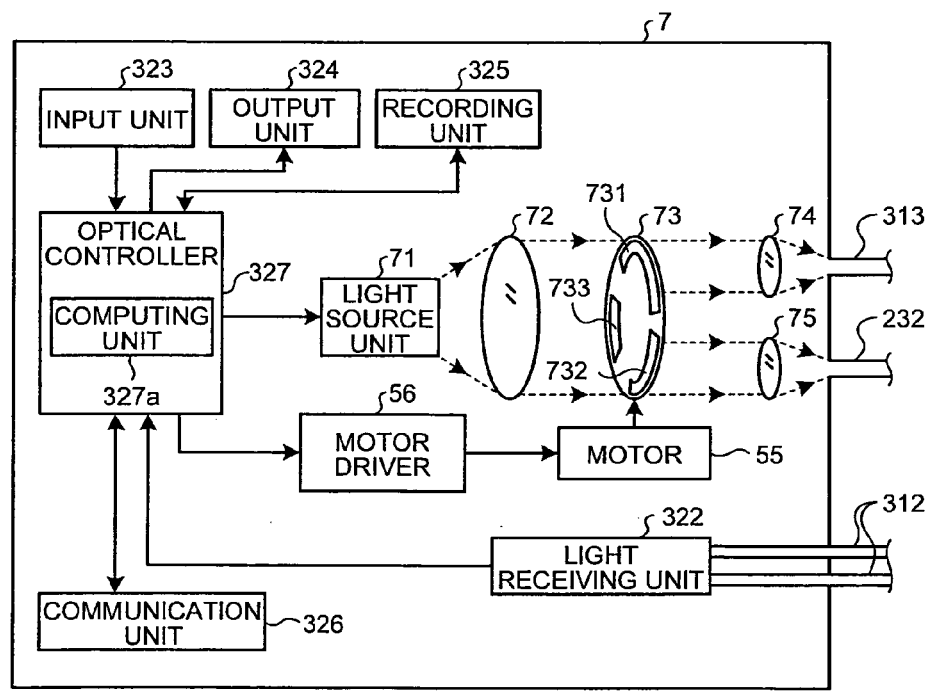
FIG. 4 is a block diagram illustrating a configuration of an optical measurement apparatus according to a second embodiment of the present invention.

FIG. 4 is a block diagram illustrating a configuration of an optical measurement apparatus according to the second embodiment of the present invention. As illustrated in FIG. 4, an optical measurement apparatus 7 has a light source unit 71, a collimator lens 72, a rotation filter 73, condenser lenses 74 and 75, the motor 55, the motor driver 56, the light receiving unit 322, the input unit 323, the output unit 324, the recording unit 325, the communication unit 326 and the optical controller 327.

The light source unit 71 is formed using, for example, a white LED or a xenon lamp. The light source unit 71 generates observation light to be supplied to the endoscope device 2 and measurement light to be supplied to the illumination fiber 311 of the measurement probe 31.

The collimator lens 72 orients light emitted by the light source unit 71 to the rotation filter 73 to be parallel.

The rotation filter 73 is arranged on the optical path of light emitted by the light source unit 71. The rotation filter 73 allows transmission of only light having a specified wavelength band among light emitted by the light source unit 71. The rotation filter 73 has a red filter 731, a green filter 732 and a blue filter 733 which allow transmission of light having wavelength bands of red light, green light and blue light. The rotation filter 73 rotates to allow sequential transmission of light having wavelength bands of red light, green light and blue light. By this means, the rotation filter 73 can emit light having wavelengths of one of red light, green light and blue light among white light emitted by the light source unit 71, at the same time, to the illumination fiber 232 of the endoscope device 2 and the illumination fiber 311 of the measurement probe 31.

The condenser lens 74 is arranged on the optical path of illumination light emitted by the light source unit 71, and condenses light having transmitted through the rotation filter 73 to emit to the illumination fiber 311 of the measurement probe 31.

The condenser lens 75 is arranged on the optical path of illumination light emitted by the light source unit 71, and condenses light having transmitted through the rotation filter 73 to emit to the illumination fiber 232 of the endoscope device 2.

Figure 5:
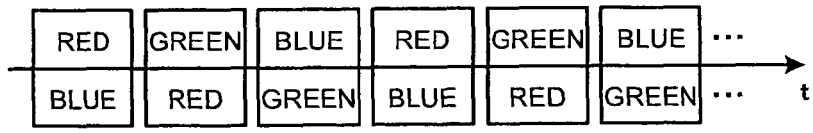
FIG. 5 is a timing chart indicating timings at which the optical measurement apparatus according to the second embodiment of the present invention radiates light of different wavelengths.

Timings of illumination light when the subject is observed in the optical measurement apparatus 7 employing the above configuration will be described. FIG. 5 is a timing chart indicating timings at which the optical measurement apparatus 7 radiates light of different wavelengths. In FIG. 5, the horizontal axis indicates a time (t).

As illustrated in FIG. 5, the optical controller 327 makes the light source unit 71 emit light, drives the motor 55 through the motor driver 56 to rotate the rotation filter 73 such that the wavelength of observation light radiated by the endoscope device 2 and the wavelength of measurement light radiated by the illumination fiber 311 of the measurement probe 31 are different from each other. By this means, it is possible to radiate observation light radiated by the endoscope device 2, on the body tissues S1 in order of wavelengths of red, green and blue, and radiate measurement light radiated by the illumination fiber 311 of the measurement probe 31 on the body tissues S1 in order of wavelengths of blue, red and green. As a result, it is possible to perform observation using the endoscope device 2 and measurement using the measurement probe 31 of the optical measurement apparatus 7 at the same time, to cancel the influence of observation light from the endoscope device 2 on measurement using the measurement probe 31, and to perform accurate measurement.

According to the above-described second embodiment of the present invention, the light source of the optical measurement apparatus 7 and the light source of the endoscope device 2 are integrally provided, so that it is possible to make the endoscope system 1 with a simple configuration.

Third Embodiment

Next, a third embodiment of the present invention will be described. In the above-described embodiments, the wavelength band of the measurement light emitted by the optical measurement apparatus and the wavelength band of the observation light emitted by the endoscope light source unit are different from each other. In the third embodiment, control is performed such that the wavelength band of the measurement light received by the optical measurement apparatus and the wavelength band of the observation light emitted by the endoscope light source device are different from each other. The same reference numeral will be used below to refer to the same components.

FIG. 6 is a block diagram schematically illustrating a configuration of an endoscope system 10 according to the third embodiment of the present invention. The endoscope system 10 shown in FIG. 6 includes the control device 4, the endoscope light source device 5, and an optical measurement apparatus 8.

The optical measurement apparatus 8 includes a measurement probe 31 and a main body unit 81. The main body unit 81 includes the input unit 323, the output unit 324, the recording unit 325, the communication unit 326, the optical controller 327, a light source unit 811, a condenser lens 812, a first collimator lens 813, a second collimator lens 814, a rotation filter 815, a first condenser lens 816, a second condenser lens 817, a light receiving unit 818, a motor 819, and a motor driver 820.

The light source unit 811 is formed using, for example, a light source, such as a white LED or a xenon lamp. The light source unit 811 generates measurement light to be emitted to the illumination fiber 311 of the measurement probe 31. The condenser lens 812 focuses the measurement light emitted by the light source unit 811 on the illumination fiber 311.

The first collimator lens 813 and the second collimator lens 814 collimate the return light emitted by the light receiving fibers 312, which are the return light caused by reflection and/or scattering of the measurement light on the body tissue S1.

The rotation filter 815 is arranged on the optical paths of return light emitted by the light receiving fibers 312. The rotation filter 815 allows transmission of only light having a specified wavelength band among the return light of the measurement light, which are the return light emitted by the light receiving fibers 312. The rotation filter 815 has a red filter 815a, a green filter 815b and a blue filter 815c which allow transmission of light having wavelength bands of red light, green light and blue light. The rotation filter 815 rotates to allow sequential transmission of light having wavelength bands of red light, green light and blue light. By this means, the rotation filter 815 can emit, to the light receiving unit 818, light having the wavelength band of any one of red light, green light and blue light among the return light of the measurement light, which are the return light emitted from the light receiving fiber 312.

The light receiving unit 818 receives and measures the return light of the measurement light emitted from the measurement probe 31, which are the return light that have transmitted the first condenser lens 816, the second condenser lens 817, and the rotation filter 815. The light receiving unit 818 is realized using a plurality of spectrometric measuring instruments and light receiving sensors. The light receiving unit 818 measures the spectrum components and intensity distribution of the return light of the measurement light emitted from the measurement probe 31 and measures each wavelength. The light receiving unit 818 outputs the measurement result to the optical controller 327.

The motor 819 is formed using, for example, a stepping motor or a DC motor, and rotates the rotation filter 815. Under control of the optical controller 327, the motor driver 820 supplies specified power to the motor 819.

In the endoscope system 10 configured as described above, the control unit 46 controls each of the light source driving controller 57 and the optical controller 327 to rotate the rotation filter 52 and the rotation filter 815 such that wavelength band of the observation light emitted by the endoscope light source device 5 and the wavelength band of the return light of the measurement light received by the light receiving unit 818 are different from each other. Specifically, the endoscope light source device 5 emits observation light having the wavelength band of red color and the optical measurement apparatus 8 receives the return light of the measurement light having the wavelength band of, for example, green color or blue color, other than the wavelength band of red color and measures the characteristics of the body tissues S1 (e.g., see FIGS. 3 and 5).

According to the above-described third embodiment of the present invention, it is possible to perform observation using the endoscope device 2 and measurement using the measurement probe 31 of the optical measurement apparatus 8 at the same time, to cancel the influence of the observation light from the endoscope device 2 on measurement using the measurement probe 31, and to perform accurate measurement.

In the above-described third embodiment of the present invention, the control unit 46 controls each of the light source driving controller 57 and the optical controller 327 to switch the endoscope light source device 5 or the rotation filter 815 such that the wavelength band of the observation light emitted by the endoscope light source device 5 and the wavelength band of the return light of the measurement light received by the light receiving unit 818 are different from each other. Alternatively, the optical controller 327 may acquire, via the control unit 46, narrow-band information on the wavelength band of the observation light emitted by the endoscope light source device 5 and, based on the acquired narrow-band information, switch the rotation filter 815 to vary the wavelength band of the return light of the measurement light, which is the return light received by the light receiving unit 818.

Fourth Embodiment

Next, a fourth embodiment of the present invention will be described. In the fourth embodiment, control is performed to switch the wavelength band of return light of measurement light used for computing by the computing unit such that the wavelength band of return light caused by reflection and/or scattering of measurement light on a biometric measurement target and the wavelength band of measurement light emitted by the endoscope light source unit are different from each other. The same reference numeral will be used below to refer to the same components.

FIG. 7 is a block diagram schematically illustrating a configuration of an endoscope system according to the fourth embodiment of the present invention. As shown in FIG. 7, an endoscope system 100 includes the control device 4, the endoscope light source device 5, and an optical measurement apparatus 9.

The optical measurement apparatus 9 includes the measurement probe 31 and a main body unit 91. The main body unit 91 includes the input unit 323, the output unit 324, the recording unit 325, the communication unit 326, the optical controller 327, a light source unit 911, a condenser lens 912, a first spectroscope 913, and a second spectroscope 914.

The light source unit 911 is formed using, for example, a light source, such as a white LED or a xenon lamp. The light source unit 911 generates measurement light to be emitted to the illumination fiber 311 of the measurement probe 31. The condenser lens 912 focuses the measurement light, which is emitted by the light source unit 911, on the illumination fiber 311.

The first spectroscope 913 and the second spectroscope 914 respectively receive return light caused by reflection and/or scattering of measurement light on the body tissues S1, emitted from the light receiving fibers 312 of the measurement probe 31. Each of the first spectroscope 913 and the second spectroscope 914 measures the spectral components of the return light caused by reflection and/or scattering on the body tissues S1 of the measurement light, which is the return light emitted from the light receiving fiber 312 of the measurement probe 31. Each of the first spectroscope 913 and the second spectroscope 914 outputs the measurement result to the optical controller 327.

Figure 8A:
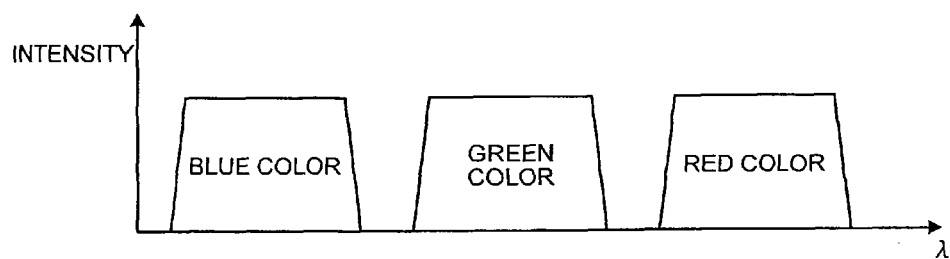
FIG. 8A is a diagram illustrating transmittance spectrum components of each filter of a rotation filter of an endoscope light source device according to the fourth embodiment of the present invention.
Figure 8B:
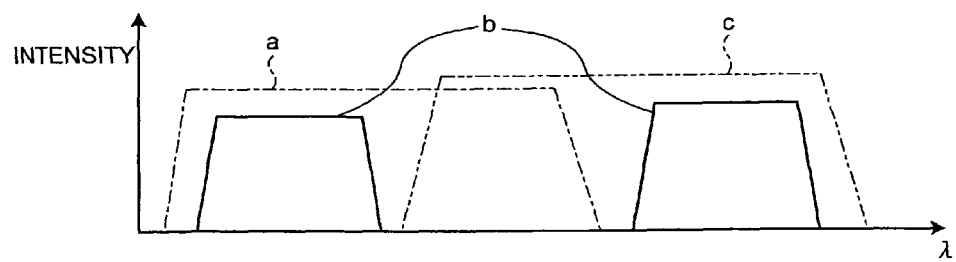
FIG. 8B is a diagram illustrating wavelength bands used for computing by a computing unit among the spectrum components that are detected by a first spectroscope and a second spectroscope of an optical measurement apparatus according to the fourth embodiment of the present invention.
Figure 9:
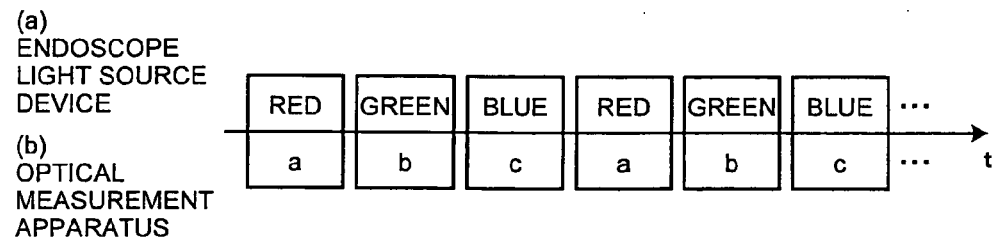
FIG. 9 is a chart indicating timings at which the endoscope light source device according to the fourth embodiment radiates observation light of different wavelength bands and timings of the wavelength bands used for computing by a computing unit among the spectrum components that are detected by the first spectroscope and the second spectroscope of the optical measurement apparatus.

Timings of observation light for observation of the subject and timings at which the computing unit 327a switches the wavelength band of the return light of the measurement light in the endoscope system 100, which is configured as described above, will be described below. FIG. 8A is a diagram illustrating transmittance spectrum components of each filter of the rotation filter 52 of the endoscope light source device 5. FIG. 8B is a diagram illustrating wavelength bands used for computing by the computing unit 327a among the spectrum components that are detected by the first spectroscope 913 and the second spectroscope 914 of the optical measurement apparatus 9. FIG. 9 is a chart indicating timings at which the endoscope light source device 5 radiates observation light of different wavelength bands and timings of the wavelength bands used for computing by the computing unit 327a among the spectrum components detected by the first spectroscope 913 and the second spectroscope 914 of the optical measurement apparatus 9. In FIGS. 8A and 8B, the horizontal axis indicates wavelength (A) and the vertical axis indicates intensity. In FIG. 9, the horizontal axis indicates time (t).

As shown in FIGS. 8A, 8B, and 9, the control unit 46 controls the light source driving controller 57 and the optical controller 327 to perform control on switching such that the wavelength band of the observation light emitted by the endoscope light source device 5 and the wavelength band of the return light used for computing by the computing unit 327a, which is the return light caused by reflection and/or scattering of the measurement light on the body tissues S1, are different from each other. Specifically, when the endoscope light source device 5 emits observation light having the wavelength band of red color, the control unit 46 causes the computing unit 327a to perform computing, by excluding the wavelength band of red color (narrow band information) from the wavelength bands of the return light of the measurement light (see FIGS. 8B and 9). By this means, it is possible to radiate observation light emitted by the endoscope light source device 5 on the body tissues S1 sequentially at the wavelengths of red, green and blue, and the computing unit 327a can compute the characteristics of the body tissues S1 by using the wavelength bands without interference of observation light from the endoscope light source device 5. As a result, it is possible to perform observation using the endoscope device 2 and measurement using the measurement probe 31 of the optical measurement apparatus 9 at the same time, to cancel the influence of observation light from the endoscope device 2 on measurement using the measurement probe 31, and to perform accurate measurement.

Figure 10:
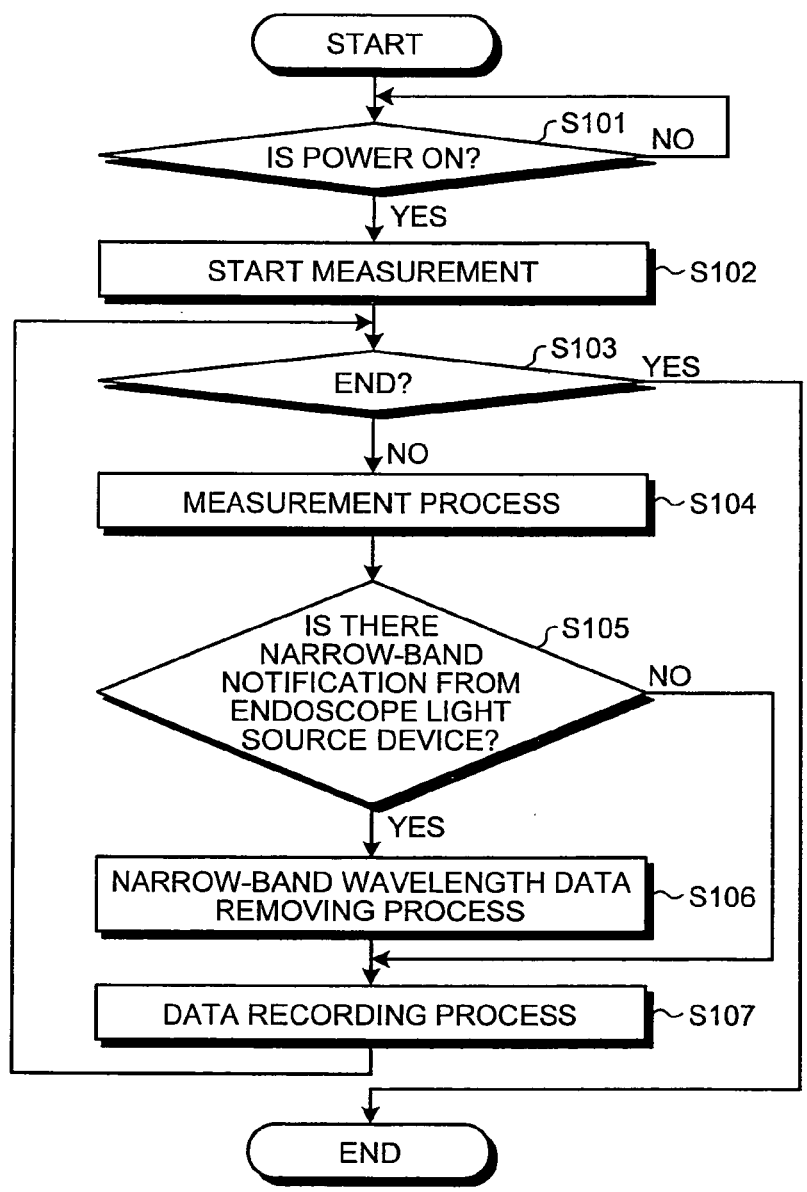
FIG. 10 is a flowchart of the outline of processing performed by the optical measurement apparatus according to the fourth embodiment of the present invention.

Next, processing performed by the optical measurement apparatus 9 will be described. FIG. 10 is a flowchart of the outline of processing performed by the optical measurement apparatus 9.

As shown in FIG. 10, once the power is on (YES at step S101), the optical measurement apparatus 9 starts measurement (step S102). In contrast, when the power is not on (NO at step S101), the optical measurement apparatus 9 repeats this determination.

The optical controller 327 determines whether an instruction signal for ending the optical measurement is input via the input unit 323 (step S103). When the optical controller 327 determines that no instruction signal for ending optical measurement is input (NO at step S103), the optical measurement apparatus 9 moves to step S104. In contrast, when the optical controller 327 determines that an instruction signal for ending optical measurement is input (YES at step S103), the optical measurement apparatus 9 ends this process.

At step S104, the optical measurement apparatus 9 performs a measurement process. Specifically, the optical measurement apparatus 9 performs a measurement process in which the light source unit 911 is caused to emit measurement light and the first spectroscope 913 and the second spectroscope 914 are caused to receive and measure the return light of the measurement light, which are return light emitted from the light receiving fibers 312.

The optical controller 327 then determines whether there is a notification on narrow band information from the endoscope light source device 5 via the control device 4 (step S105). When the optical controller 327 determines that there is a notification on narrow-band information from the endoscope light source device 5 via the control device 4 (YES at step S105), the optical measurement apparatus 9 moves to step S106.

The computing unit 327a then performs a narrow-band data removing process for computing the characteristics of the body tissues S1 by removing the components of the narrow-band wavelength of the observation light emitted by the endoscope light source device 5 from the wavelength band of the return light of the measurement light, which are the return light output from the first spectroscope 913 and the second spectroscope 914, respectively (step S106), and the computing unit 327a performs data recording process for recording the computing results in the recording unit 325 (step S107). The optical measurement apparatus 9 then goes back to step S103.

At step S105, when the optical controller 327 determines that there is no notification on narrow band information from the endoscope light source device 5 via the control device 4 (NO at step S105), the optical measurement apparatus 9 moves to step S107.

According to the above-described fourth embodiment of the present invention, the control unit 46 controls each of the light source driving controller 57 and the optical controller 327 to compute the characteristics of the body tissues S1 by removing the components of the observation light of the wavelength band emitted by the endoscope light source device 5 from the return light of the measurement light used for computing by the computing unit 327a. As a result, it is possible to perform observation using the endoscope device 2 and measurement using the measurement probe 31 of the optical measurement apparatus 9 at the same time, to cancel the influence of observation light of the endoscope device 2 on measurement using the measurement probe 31, and to perform accurate measurement.

In the fourth embodiment, the control unit 46 controls each of the light source driving controller 57 and the optical controller 327 to compute the characteristics of the body tissues S1 by removing the components of the observation light of the wavelength band emitted by the endoscope light source device 5 from the return light of the measurement light used for computing by the computing unit 327a. Alternatively, the optical controller 327 may acquire narrow-band information on the wavelength bands of the observation light emitted by the endoscope light source device 5 via the control unit 46 and, based on the acquired narrow-band information, may remove the components of the observation light of the wavelength band emitted by the endoscope light source device 5 from the return light of the measurement light used for computing by the computing unit 327a.

Fifth Embodiment

Next, a fifth embodiment of the present invention will be described below. In the fifth embodiment, an endoscope light source device radiates observation light by a simultaneous method. The same reference numeral will be used below to refer to the same components.

Figure 11:
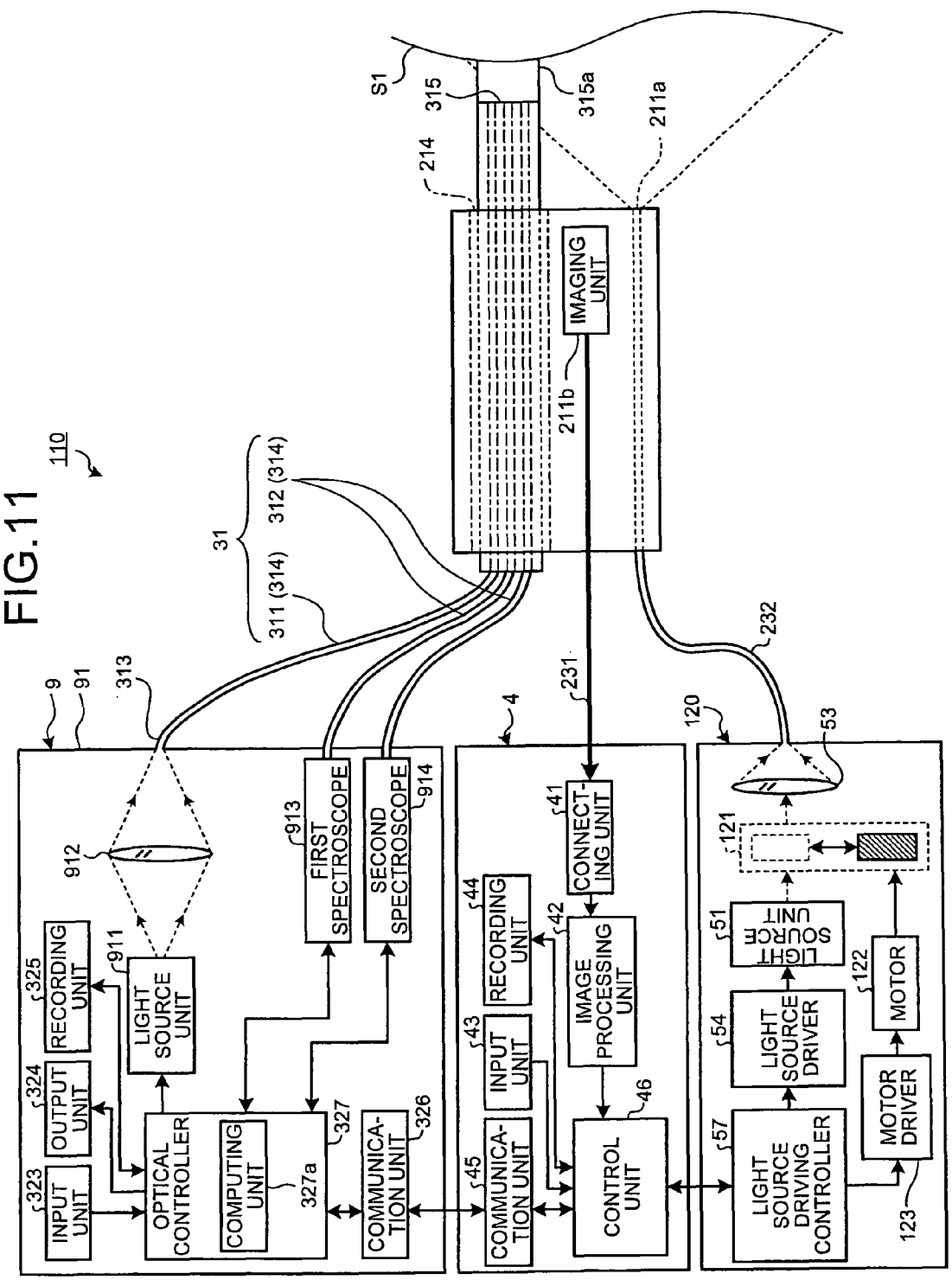
FIG. 11 is a block diagram schematically illustrating a configuration of an endoscope system according to a fifth embodiment of the present invention.

FIG. 11 is a block diagram schematically illustrating a configuration of an endoscope system 110 according to the fifth embodiment of the present invention. As shown in FIG. 11, the endoscope system 110 includes the control device 4, the optical measurement apparatus 9, and an endoscope light source device 120.

The endoscope light source device 120 includes the condenser lens 53, the light source driver 54, the light source driving controller 57, a narrow-band filter 121, a motor 122, and a motor driver 123.

Figure 12:
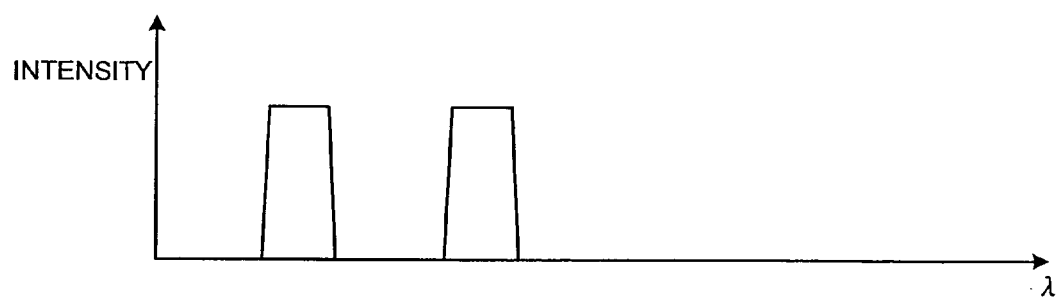
FIG. 12 is a diagram illustrating transmittance spectrum components of a narrow-band filter of an endoscope light source device of the endoscope system according to the fifth embodiment of the present invention.

The narrow-band filter 121 allows transmission of only light of specified wavelength bands among observation light emitted by the light source unit 51. Specifically, as shown in FIG. 12, the narrow-band filter 121 allows transmission of the narrow-banded components of G (green) and B (blue). The narrow-banded light includes, for example, NBI (Narrow Band Imaging) light of two types of bands: blue light (e.g., 400 nm to 500 nm) and green light (e.g., 500 nm to 600 nm) that are narrow-banded such that the light is easily absorbed in the hemoglobin in the blood.

The motor 122 is formed using, for example, a stepping motor or a DC motor, and moves the narrow-band filter 121 to the optical path of the observation light emitted by the light source unit 51 or evacuates the narrow-band filter 121 from the optical path of the observation light. Under control of the light source driving controller 57, the motor driver 123 supplies specified power to the motor 122.

Figure 13:
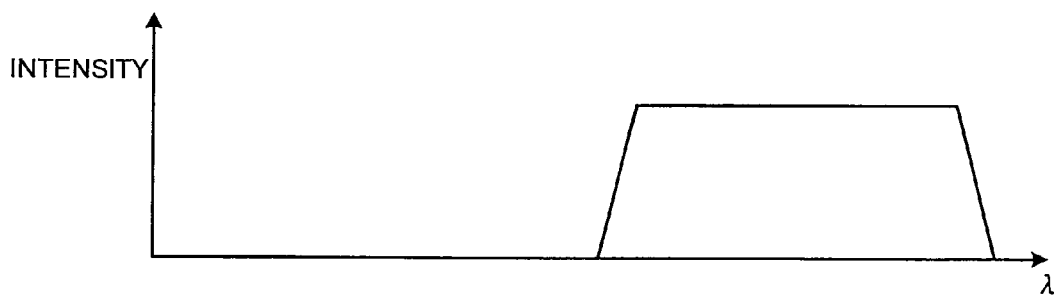
FIG. 13 is a diagram illustrating spectrum components used for computing by a computing unit among the wavelength bands of return light of measurement light received by a first spectroscope and a second spectroscope when the endoscope light source device of the endoscope system according to the fifth embodiment of the present invention emits observation light.

Timings of observation light when the subject is observed and timings at which the frequency band of the return light of the measurement light used when the computing unit 327a performs computing in the endoscope system 110 configured as described above will be described above. FIG. 13 is a diagram indicating the spectrum component used for computing by the computing unit 327a among the wavelength bands of the return light of the measurement light, which are the return light received by the first spectroscope 913 and the second spectroscope 914. In FIG. 13, the horizontal axis indicates wavelength (λ).

As shown in FIG. 13, the control unit 46 controls the light source driving controller 57 and the optical controller 327 to perform control for switching the wavelength band of the return light caused by reflection and/or scattering of the measurement light on the body tissues S, which is the wavelength band used when the computing unit 327a performs computing, such that the wavelength band is different from the wavelength band of the observation light emitted by the endoscope light source device 120. Specifically, when the endoscope light source device 120 is emitting narrow-band observation light, the control unit 46 causes the computing unit 327a to perform computing by excluding the narrow band from the wavelength band of the return light of the measurement light (see FIG. 13). Accordingly, it is possible to perform observation using the endoscope light source device 120 and measurement using the measurement probe 31 of the optical measurement apparatus 9 at the same time, to cancel the influence of observation light from the endoscope light source device 120 on measurement using the measurement probe 31, and to perform accurate measurement.

Figure 14:
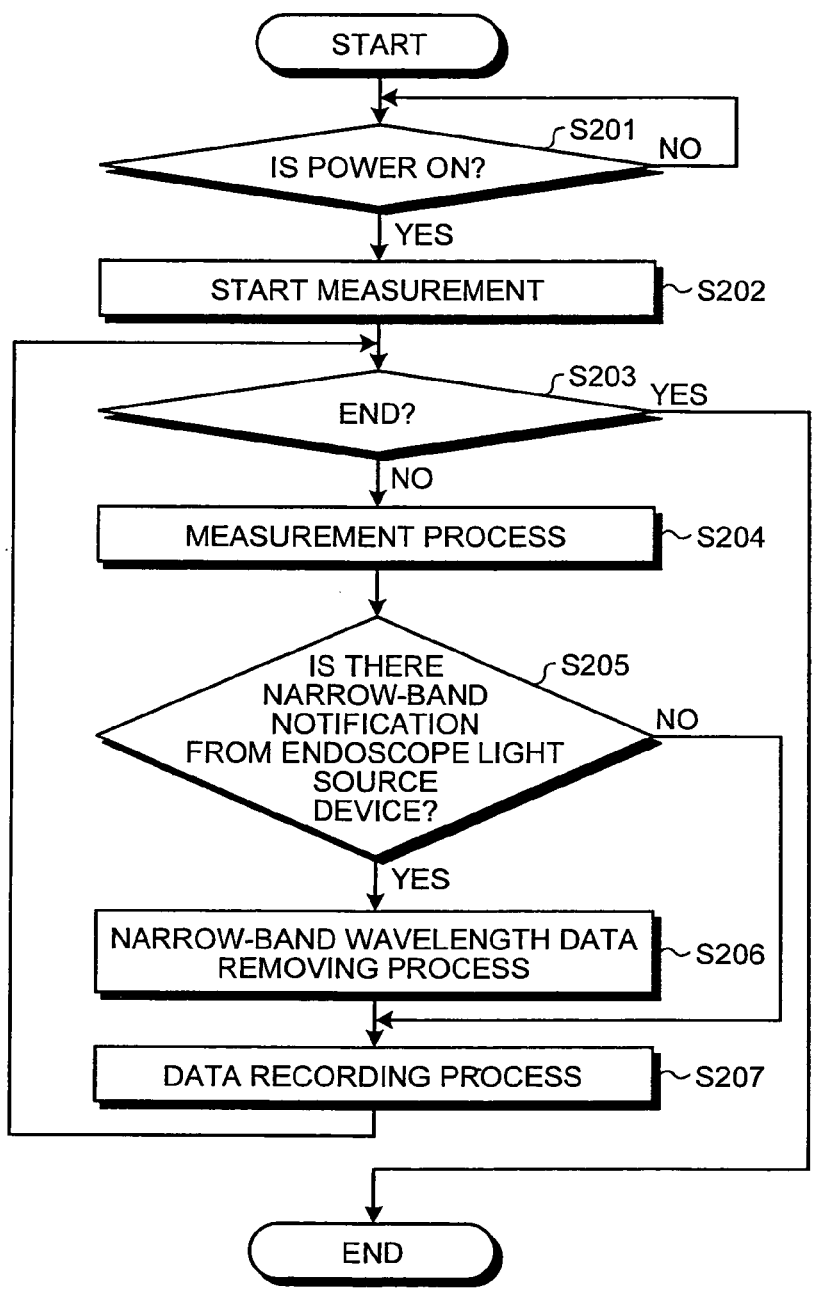
FIG. 14 is a flowchart of the outline of processing performed by the optical measurement apparatus of the endoscope system according to the fifth embodiment of the present invention.

Next, processing performed by the endoscope system 110 will be described. FIG. 14 is a flowchart of the outline of processing performed by the optical measurement apparatus 9.

Steps S201 to S207 correspond to steps S101 to steps S107, respectively.

According to the above-described fifth embodiment of the present invention, the control unit 46 controls each of the light source driving controller 57 and the optical controller 327 to compute the characteristics of the body tissues S1 by removing the components of the observation light of the narrow band, which is the observation light emitted by the endoscope light source device 120, from the return light of the measurement light used for computing by the computing unit 327a. As a result, it is possible to perform observation using the endoscope device 2 and measurement using the measurement probe 31 of the optical measurement apparatus 9 at the same time, to cancel the influence of the observation light of the endoscope device 2 on measurement using the measurement probe 31, and to perform accurate measurement.

According to the above-described fifth embodiment, the control unit 46 controls each of the light source driving controller 57 and the optical controller 327 to compute the characteristics of the body tissues S1 by removing the components of the observation light of the wavelength bands emitted by the endoscope light source device 120 from the return light of the measurement light used for computing by the computing unit 327a. Alternatively, the optical controller 327 may acquire narrow-band information on the wavelength bands of the observation light emitted by the endoscope light source device 120 via the control unit 46 and, based on the acquired narrow-band information, may remove the components of the observation light of the wavelength bands emitted by the endoscope light source device 120 from the return light of the measurement light used for computing by the computing unit 327a.

Reference Example

Although the optical measurement apparatus according to the above embodiments radiate light of different wavelength bands, by radiating light of one wavelength band, it is possible to cancel the influence of illumination light from the endoscope device 2 on measurement using the measurement probe 31 and perform accurate measurement.

Figure 15:
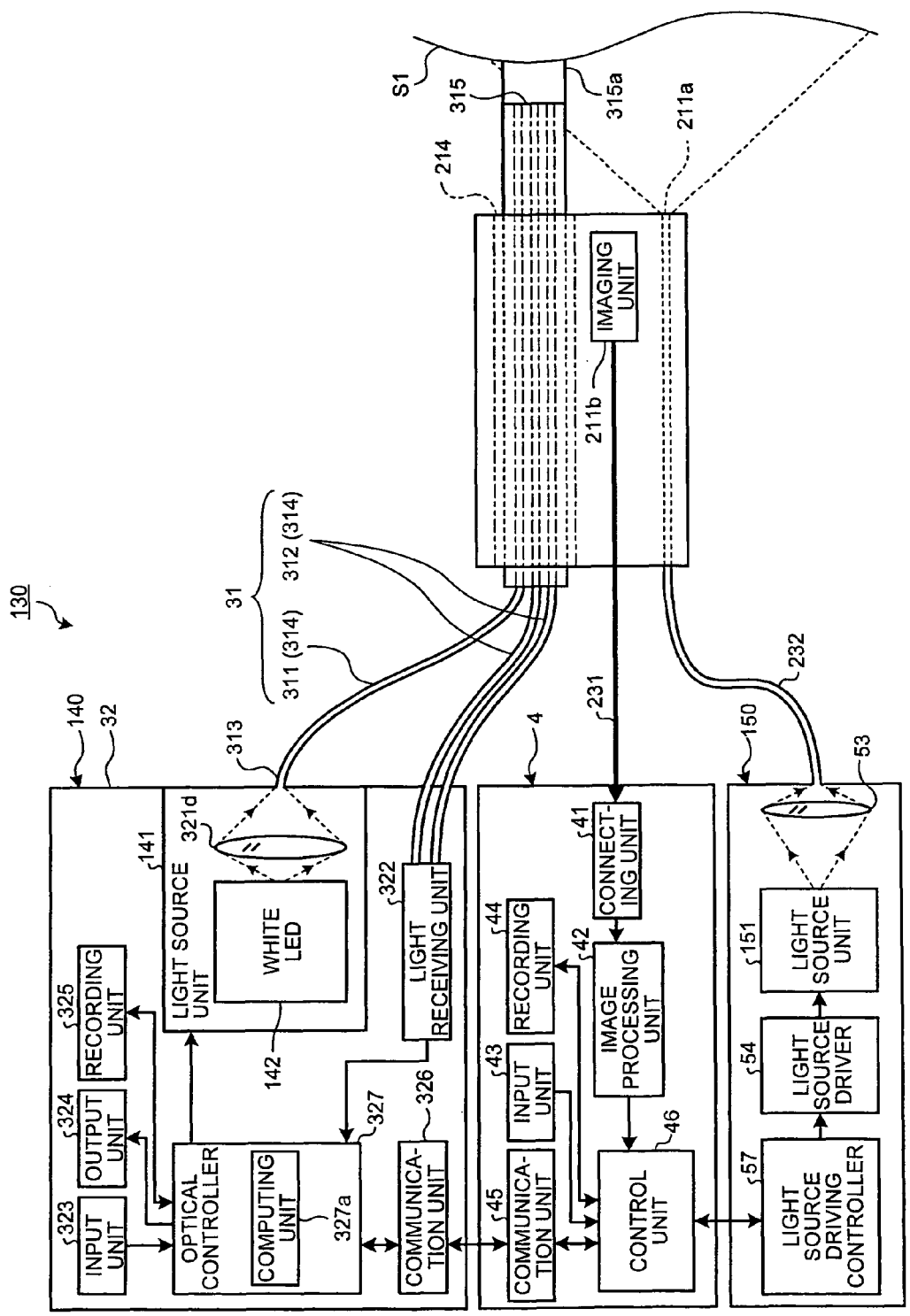
FIG. 15 is a block diagram illustrating a configuration of an endoscope system according to a reference example related to the embodiments of the present invention.

FIG. 15 is a block diagram illustrating a configuration of an endoscope system 130 according to a reference example of the embodiment of the present invention. In addition, in FIG. 15, elements employing the same configurations as in the endoscope system described in the above embodiments will be assigned the same reference numerals, and will not be described.

As illustrated in FIG. 15, the endoscope system 130 has the control device 4, an optical measurement apparatus 140 and an endoscope light source device 150.

The optical measurement apparatus 140 has the light receiving unit 322, the input unit 323, the output unit 324, the recording unit 325, the communication unit 326, the optical controller 327, and a light source unit 141. The light source unit 141 has a white LED 142 which emits white light and the condenser lens 321d.

The endoscope light source device 150 has the condenser lens 53, the light source driver 54, the light source driving controller 57, and a light source unit 151. The light source unit 151 is formed using, for example, a white LED or a xenon lamp.

Figure 16:
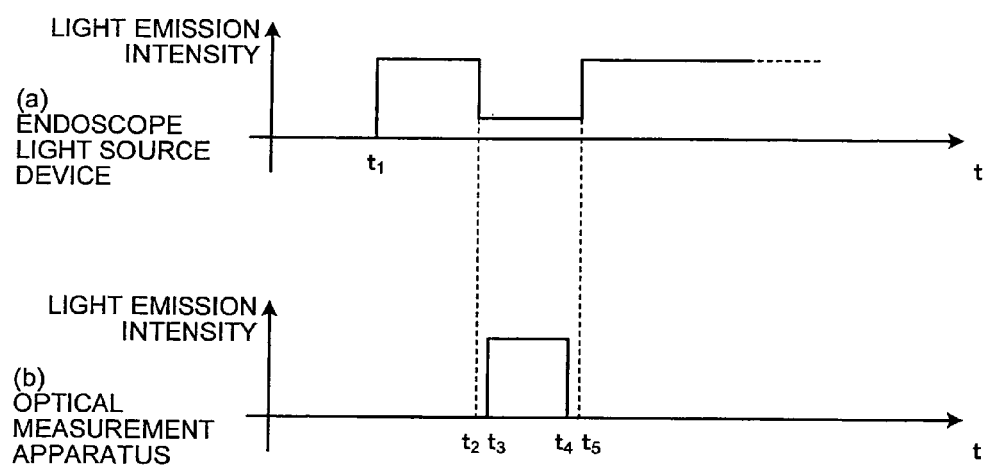
FIG. 16 is a timing chart indicating timings at which an optical measurement apparatus and an endoscope light source device according to the reference example related to the embodiments of the present invention respectively radiate illumination light.

Timings of illumination light radiated respectively by the optical measurement apparatus 140 and the endoscope light source device 150 when the endoscope system 130 employing the above configuration performs observation will be described. FIG. 16 is a timing chart indicating timings at which the optical measurement apparatus 140 and the endoscope light source device 150 respectively radiate illumination light. In FIG. 16, the horizontal axis indicates a time (t), and the vertical axis indicates the light emission intensity.

As illustrated in FIG. 16, the control unit 46 transmits a drive signal for radiating observation light on the body tissues S1, to the light source driving controller 57. In this case, the light source driving controller 57 drives the light source unit 151 to emit white light (time t1).

Subsequently, in a period (time t2 to time t5) in which the optical measurement apparatus 140 performs optical measurement, the control unit 46 transmits a command signal for decreasing the light emission intensity of the light source unit 151 to a level which does not influence optical measurement using the optical measurement apparatus 140, to the light source driving controller 57, and transmits a drive signal for radiating measurement light of white light on the body tissues S1, to the optical controller 327 of the optical measurement apparatus 140. In this case, by decreasing power to be supplied to the light source unit 151, the light source driving controller 57 decreases the intensity of observation light emitted by the light source unit 151 to a level which does not influence optical measurement using the optical measurement apparatus 140 (time t2). By contrast with this, the optical controller 327 drives the white LED 142 of the light source unit 141 to emit measurement light (time t4). In this case, although observation light radiated by the endoscope light source device 150 decreases, the image sensor of the distal end portion 211 can capture a normal observation image of the interior of the subject.

Subsequently, the control unit 46 transmits a stop signal for stopping emission of light, to the optical controller 327 of the optical measurement apparatus 140, and transmits a drive signal for returning the light emission intensity of the light source unit 151 back to the original emission intensity, to the light source driving controller 57. In this case, the optical controller 327 stops emission of light from the light source unit 141 (time t4). By contrast with this, the light source driving controller 57 returns the power to be supplied to the light source unit 151, to the original power to return the intensity of the observation light emitted by the light source unit 151 to the original intensity (time t5).

According to the above-described reference example of the embodiments of the present invention, in a measurement period (time t2 to time t5) of the optical measurement apparatus 140, the control unit 46 decreases the light emission intensity of illumination light emitted by the light source unit 151 of the endoscope light source device 150. By this means, it is possible to decrease the influence of observation light from the endoscope light source device 150 on measurement using the optical measurement apparatus 140, and perform accurate measurement.

Further, according to the reference example of the embodiments of the present invention, when measurement using the optical measurement apparatus 140 is performed, illumination light of the endoscope light source device 150 is not stopped, so that it is possible to perform the operation of the measurement probe 31 and measurement while checking a normal observation image.

In addition, although, with the above-described reference example related to the embodiments of the present invention, in the measurement period (time t2 to time t5) of the optical measurement apparatus 140, the control unit 46 decreases the light emission intensity of observation light emitted by the light source unit 151 of the endoscope light source device 150, when the measurement period of the optical measurement apparatus 140 ends in one frame of the image sensor or less, observation light emitted by the light source unit 151 of the endoscope light source device 150 may be stopped or blocked.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope system comprising:
    an endoscope which includes an insertion tube configured to be inserted into an inside of a subject and which is configured to capture an image of the inside of the subject by an imaging unit provided in the insertion tube and generate an image signal;
    an optical measurement apparatus including a measurement probe configured to be inserted into the inside of the insertion tube;
    an endoscope light source configured to switch between observation light of a plurality of wavelengths and output the observation light to observe a target object via the insertion tube;
    a probe light source configured to output measurement light to measure characteristics of the target object via the measurement probe;
    a spectroscope configured to receive and disperse return light via the measurement probe, the return light being caused by at least one of reflection and scattering of the measurement light from the target object; and
    an optical controller configured to compute the characteristics of the target object based on results of dispersion by the spectroscope; and
    a central processing unit (CPU) configured to control the optical controller to remove, from the return light, a component of the wavelength band of the observation light outputted by the endoscope light source to compute the characteristics of the target object.

2. An optical measurement apparatus that includes a measurement probe configured to be inserted through an insertion tube of an endoscope, and is configured to perform bidirectional communication with a control device for controlling an endoscope light source configured to switch between observation light of a plurality of wavelengths and output the observation light to the endoscope, the optical measurement apparatus comprising:
    a probe light source configured to output measurement light to measure characteristics of a target object via the measurement probe;
    a spectroscope configured to receive and disperse return light via the measurement probe, the return light being caused by at least one of reflection and scattering of the measurement light from the target object;
    an optical controller configured to compute the characteristics of the target object based on results of dispersion by the spectroscope; and
    an CPU configured to control the optical controller to remove, from the return light, a component of the wavelength band of the observation light outputted by the endoscope light source to compute the characteristics of the target object.

* * * * *